(12) United States Patent
Dupont

(10) Patent No.: US 7,759,325 B2
(45) Date of Patent: Jul. 20, 2010

(54) USE OF LECITHIN AS A MEDICATION FOR THE TREATMENT OF PSORIASIS

(75) Inventor: Paul Dupont, Toulouse (FR)

(73) Assignee: SC Dicophar, Colomiers (FR)

( * ) Notice: Subject to any disclaimer, the term of this patent is extended or adjusted under 35 U.S.C. 154(b) by 78 days.

(21) Appl. No.: 11/911,743

(22) PCT Filed: Apr. 11, 2006

(86) PCT No.: PCT/FR2006/000792

§ 371 (c)(1),
(2), (4) Date: Oct. 17, 2007

(87) PCT Pub. No.: WO2006/111633

PCT Pub. Date: Oct. 26, 2006

(65) Prior Publication Data

US 2008/0153782 A1    Jun. 26, 2008

(30) Foreign Application Priority Data

Apr. 18, 2005  (FR) .................................. 05 03827
Jun. 27, 2005  (FR) .................................. 05 06496

(51) Int. Cl.
*A61K 31/685* (2006.01)
(52) U.S. Cl. ....................................................... 514/78
(58) Field of Classification Search .................... 514/78
See application file for complete search history.

(56) References Cited

U.S. PATENT DOCUMENTS 5,091,171 A * 2/1992 Yu et al. ...................... 424/642
6,248,340 B1 * 6/2001 Maor et al. .................. 424/401
2002/0012648 A1 1/2002 Orthoefer

FOREIGN PATENT DOCUMENTS

WO     9842342     10/1998
WO     2005002591   1/2005

OTHER PUBLICATIONS

Escobar et al, "Topical Fish Oil in Psoriasis-A Controlled and Blind Study", Blackwell Scientific Publications, Oxford, GB, vol. 17, No. 3, 1992, pp. 159-162.
Mayser et al, "[omega]-3 Fatty Acid-based Lipid Infusion in Patients with . . . Multicenter Trial", Journal of the Amer. Academy of Dermatology, 1998, US, vol. 38, No. 4, 1998, pp. 539-547.

* cited by examiner

*Primary Examiner*—Kevin Weddington
(74) *Attorney, Agent, or Firm*—Dennison, Schultz & MacDonald

(57) ABSTRACT

Methods and compositions for the prevention and treatment of recent and old dermatitis, especially psoriasis, using lecithin or a lecithin-rich extract. According to one embodiment, phospholipids constituting the lecithin are esterified by Omega 3-type polyunsaturated fatty acids, in particular by docosahexaensic acid (DHA) and eicosapentaenoic acid (EPA) or by an alkyl glycerol. The lecithin can be of marine origin, extracted from a marine organisms such as fish, shrimp, krill, zooplankton, algae, and phytoplankton, which are advantageous in that their phospholipids, especially phosphatidylcholine, are naturally esterified by Omega 3 fatty acids, and essentially by DHA and EPA.

9 Claims, No Drawings

USE OF LECITHIN AS A MEDICATION FOR THE TREATMENT OF PSORIASIS

This invention relates to the use of lecithin for the formulation of a pharmaceutical composition, useful for the prevention and the treatment of recent or ancient dermatitis, especially psoriasis.

Abnormal scaly or keratosic formations of the dermis are one of the manifestations of the skin condition, which can be found in many dermatoses, recently appearing or chronic, and especially in the various types of psoriasis.

Psoriasis is an erythemo-scaly dermatitis of chronic evolution, characterized by thickened patches of reddish skin covered by slivery-white scales, which affects an estimated 2 percent of the population. With 60 000 new cases diagnosed each year, it is one of the most prevalent skin diseases. It appears as painful itching and cracked and bleeding skin, which can affect over 10 percent of the body surface. In its common form, it is typically found on the elbows, on the ulnar edge of the forearms, on knees, lower back, scalp and nails. Some particular forms considered to be severe psoriasis are also known, such as erythrodermic psoriasis, psoriatic arthritis or pustular psoriasis. About 1.5 percent people develop psoriasis during childhood, before age 10, and 35 percent before age 20. This abnormality of the epidermis renewal is thus a serious affection, representing an important Public Health concern.

The cause of psoriasis is as yet unknown, however the factors implicated are reckoned to be multiple. A genetic predisposition has been identified, with 30 percent of the cases having a family history of psoriasis, as well as environmental factors. Psychological factors can often trigger flare-ups. Psoriatic lesions may also develop around skin injury sites, such as scrapes, vaccinations, surgery. Alcohol and tobacco appear to be linked to the severity of the disease, and can cause resistance to the treatment's benefits.

The disease is of chronic evolution, and usually occurs in the form of unpredictable outbreaks, interrupted by remissions during which the lesions are minor.

Even in the less severe forms, and though the general condition of the patient is not altered in the common forms, psoriasis is a disease which can heavily affect the quality of life when the lesions are visible or prevent manual work, consequences that are often underestimated by the physician.

For the time being, physicians can rely on systemic treatments which provide transitory results, but not yet on curative treatment.

Topical treatments, in the form of ointments and creams, are based on cortisone and vitamin D derivatives, these two substances being often combined. Retinoids (vitamin A derivative) may also be used. These are very useful, but they are only suitable for small lesions, or for a psoriasis of slow progression. If the lesions cover more than 10 percent of the body surface, more than a half of the patients stop following these demanding treatments after one month, for lack of time. Moreover, vitamin D derivatives are potentially irritating and, especially corticoids can cause an atrophy of the skin, and may lead to rebounds of the disease.

Phototherapy is efficient in many patients. It consists in a controlled exposure to UVB and UVA, combined with a light-sensitizing medication. The cures are demanding, because the patients have to submit to three sessions of two hours weekly, over a period of 8 to 10 weeks. This technique has the major disadvantage of inducing an increased risk of skin cancer in the long term, as well as an accelerated ageing of the skin. It is therefore essential to observe very strict rules.

For the patients who are not responding to either topical treatments or phototherapy, that is, 30 percent to 40 percent, systemic therapy can be prescribed. One of these treatments lies on the oral intake of retinoid, usually combined with phototherapy or with an intake of methotrexate (Novatrex®) which is the reference treatment. This medication having undesirable side effects, particularly on the liver and blood, its prescription must be carefully monitored by a doctor. Cidosporine (Neoral®) is also very efficient, but due to its renal toxicity, it can't be prescribed for long lasting treatments.

One can understand that the treatments recommended so far ail have important limits concerning their indication and tolerance, and that their efficiency is uncertain and temporary in many cases.

At this point, the present inventor has carried out trials, with the aim of identifying a substance capable of being applied in the treatment of dermatitis or any skin disease, appearing in the form of, or provoked by abnormal scaly and/or keratosic formations of the dermis, these being acute or chronic. Surprisingly and unexpectedly, it has been discovered that the administration of a composition based on lecithin to a patient suffering from such a disease led to excellent results, what has ended in this invention.

This is the reason why the object of this invention is to provide a composition, useful for the curative treatment of conditions induced by, or appearing in the form of abnormal scaly and/or keratosic formations of the dermis, such as these occurring in recent or chronic dermatitis, especially in the various forms of psoriasis. A prophylactic action is also sought.

Unexpectedly, it has been discovered that lecithin-based compositions enabled the formulation of such a product. The invention thus lies in the use of lecithin or of a lecithin rich extract to formulate such a medication, effective for the prevention and the treatment of dermatitis and other recent or chronic dermis diseases, which doesn't have undesirable side effects and of which form is easy to use for the patient. The therapeutic compositions are also the purpose of this invention.

Lecithin is a natural emulsifier which has been known for a long time, abundant in egg yolk and in the nervous tissues. It is considered an essential substance for the good functioning of the cardiovascular system, brain, nervous system, liver and many other organs.

According to common usage, the term "lecithin" refers to any complex essentially composed of natural phospholipids (or phosphoglycerides), that is essentially phophatidylcholine, phosphatidylinositol, phosphatidylethanolamine, phosphatidyl serine and sphingomyeline.

Besides, these phosphoglycerides can be esterified on the free primary alcohol function, by saturated or unsaturated fatty acids. These fatty acids can more particularly be polyunsaturated fatty acids of the Omega 3 type, especially docosahexanoic acid (DHA), eicosapentaenoic acid (EPA), docosapentaenoic acid (DPA). It may also be a fatty acid of the alkyl-glycol type. The distribution profile of these various phospholipids and of their esterified derivatives can vary from an organism to another.

Lecithin can be extracted from plants, such as soya beans, or from animals, especially fish. The extraction methods are known per se. Lecithin is commonly used in animals' food and as a food complement in human dietetics.

However, its action as a therapy for skin diseases was totally unknown. The unexpected effect of lecithin has been brought out for the first time by the actual inventor. Marine lecithins, that is lecithins extracted from marine organisms, have proven particularly interesting for the realization of the actual invention.

A first object of this invention is the use of lecithin in a composition designated to the formulation of a medication, useful in the prevention and the treatment of conditions induced by, or manifesting through abnormal scaly or keratosic formations of the dermis.

In particular, said utilisation applies to the conditions selected from a group comprising common psoriasis, guttate psoriasis, nummular psoriasis, plaque psoriasis, erythrodermic psoriasis, psoriatic arthritis, pustular psoriasis, child psoriasis, parapsoriasis, acute or chronic dermatitis such as ichtiosis and keratose dermatitis including palmoplantar keratoderma.

According to a specific aspect of this invention, the extract contains lecithin in an amount ranging from 10 percent to 50 weight percent weight, in a fatty phase. Preferably, lecithin is found in an amount of 20 weight percent in the extract. Lecithin extract appears in the form of an oily liquid which can vary in color from yellow to brown depending on its origin, and taking a brown orange shade when of fish origin. It oxidizes easily. Its oleic acidity is 0.1 percent, its iodine number 170, and its maximum peroxide value 5 meq/kg. It is non toxic at the dosage used, in animal as in human beings.

In another aspect of the present invention, lecithin comprises the following phospholipids, at a weight ratio expressed as a proportion of the total weight of the lecithin's phospholipids from 10% to 75% phosphatidylcholine, preferably 45%
from 10% to 30% phosphatidylinozitol, preferably 16%
from 5% to 30% phosphatidylethanolamine, preferably 20%
from 5% to 20% phosphatidylserine, preferably 5%
from 5% to 30% sphingomyeline, preferably 5%.

In a particular aspect of the present invention, lecithin comprises the following phospholipids, at a weight ratio expressed as a proportion of the total weight of the lecithin's phospholipids 45% phosphatidylcholine,
5-16% phosphatidylinozitol,
20% phosphatidylethanolamine,
10% phosphatidylserine,
5% sphingomyeline.

According to an advantageous characteristic of the present invention, said phospholipids are esterified by the omega 3-type polyunsaturated fatty acids. Actually, a primary alcohol function is present in the phospholipids mentioned above, which can thus participate to an esterification reaction with an acid, the omega 3-type polyunsaturated acids being preferred.

According to a preferred aspect of the present invention, said phospholipids are esterified by the following omega 3-type fatty acids, within the range expressed by weight out of the total weight of said fatty acids:

by docosahexaenoic acid (DHA) within the range of 15% to 85%
by eicosapentaenoic acid (EPA) within the range of 5% to 35%
by docosapentaenoic acid (DPA) within the range of 0.5% to 5%
by a fatty acid of the alkyl glycerol type within the range of 5% to 30%

As a general rule, phospholipids are mainly esterified by the DHA.

According to a particular aspect of the use according to this invention, the said phospholipids are esterified, by the following fatty acids which are present by weight expressed as a proportion of the total weight of said fatty acids by docosahexaenoic acid (DHA) for at least 17%
by eicosapentaenoic acid (EPA) for at least 14%
by docosapentaenoic acid (DPA) for at least 0.5%
by the fatty acid of the alkyl glycerol type for at least 5%.

According to an interesting characteristic of the use according to this invention, lecithin is extracted from a marine organism selected from a group comprising fish, shrimps, krill, zooplankton, algae, phytoplankton or a blend of these. It is then called a "marine lecithin." Its particular advantage lies in the fact that its phospholipids, especially phosphatidylcholine, are naturally esterified by omega 3-type fatty acids, and essentially by DHA and EPA. By extension, one can consider using egg lecithin, artificially enriched in fatty acids.

The fish are preferably of cold sea origin, as well as krill which is a cold water plankton composed of small transparent crustaceans (essentially Euphausia Superba), constituting the greater part of blue whales' diet.

According to a preferred embodiment of this invention with a lecithin extract, the said fatty phase is a fish oil, preferably a fish oil rich in omega 3. As an alternative, the lecithin employed for the use according to the invention can also take the form of purified lecithin powder.

Finally, the said medication can advantageously have a lecithin content of about 5% to 50%, preferably within the range of about 10% to 30% by weight. The medication can be used at a dosage allowing the intake of an efficient dose, which is ranging between 0.4 g and 2 g lecithin daily. The oral form is preferred, because the intake induces very little constraint, what allows a good tolerance in patients for cures lasting several months.

Another object of this invention concerns a therapeutic composition, useful for the treatment of conditions induced by, or appearing in the form of abnormal scaly and/or keratosic formations of the dermis, containing lecithin or a lecithin extract as an active principle. In particular, the composition consistent with the invention is indicated in the prevention and the treatment of skin disorders selected from the group consisting of common psoriasis, guttate psoriasis, nummular psoriasis, plaque psoriasis, erythrodermic psoriasis, psoriatic arthritis, pustular psoriasis, child psoriasis, parapsoriasis, acute or chronic dermatitis.

According to an interesting characteristic, in the therapeutic composition according to this invention, lecithin contains the following phospholipids, by weight expressed as a proportion of the total weight of the lecithin's phospholipids:

from 10% to 75% phosphatidylcholine, preferably 45%
from 10% to 30% phosphatidylinositol, preferably 16%
from 5% to 30% phosphatidylethanolamine, preferably 20%
from 5% to 20% phosphatidylserine, preferably 5%
from 5% to 30% sphingomyeline, preferably 5%.

Preferably, lecithin comprises the following phospholipids, by weight expressed as a proportion of the total weight of the lecithin's phospholipids 45% phosphatidylcholine,
16% phosphatidylinositol,
20% phosphatidylethanolamine,
10% phosphatidylserine,
5% sphingomyeline.

According to another interesting characteristic, in the therapeutic composition according to this invention, the said phospholipids are esterified by omega 3-type polyunsaturated fatty acids.

Preferably, said phospholipids are esterified by, in a part with respect to the total weight of said fatty acids:

docosahexaenoic acid (DHA) within the range of 15% to 85%
eicosapentaenoic acid (EPA) within the range of 5% to 35%
docosapentaenoic acid (DPA) within the range of 0.5% to 5%
a fatty acid of the alkyl glycerol type within the range of 5% to 30%.

According to an also preferred embodiment, said phospholipids are esterified, by, in a part with respect to the total weight of said fatty acids:
docosahexaenoic acid (DHA) for at least 17%
eicosapentaenoic acid (EPA) for at least 14%
docosapentaenoic acid (DPA) for at least 0.5%
the fatty acid of the alkyl glycerol type for at least 5%.

According to a particular embodiment of this invention, the therapeutic composition consistent with the invention contains lecithin extracted from a marine organism selected from the group consisting of fish, shrimp, krill, zooplankton, algae, phytoplankton or a mixture of these.

According to another particular embodiment of the therapeutic composition consistent with the invention, lecithin is brought in the form of an extract in a fatty phase, the said phase being fish oil, preferably a fish oil rich in omega 3.

The medication formulated with the composition containing lecithin, can be administered in the form of a product to be taken by oral or rectal route or by injection. The oily extract, as well as the purified forms can be encapsulated. The composition according to the invention may also be presented in any form, such as capsules, pills, suppositories, pessaries, cream, lotion, milk, ointment, gel or powder.

If necessary, the medication may also contain an excipient suitable for an oral, rectal or direct lymphatic administration. This will be the case more particularly in topical compositions. Such an excipient can be judiciously selected by the specialist among the excipients of therapeutic use which are neutral towards the actives, according to the chosen way of administration and to the wished final texture. For instance, one can use water, propylene glycol, butylene glycol, ethoxylated or propoxylated diglycerols.

The lecithin or lecithin extract used according to the present invention can of course be completed by other components such as additives or vectorisation supports, according to techniques known by the expert. The additives can be, for instance, those necessary to an acceptable formulation of the medication containing lecithin, such as thickeners, surfactants, antioxidants, colours, preservatives, perfumes. The vectorisation may be performed by solubilizing in liposomes, adsorption on powdery organic polymers or on mineral supports such as talc or betonies, or with the support of any other pharmaceutically acceptable vector.

The object of the present, as well as the possible ways to use it and its advantages, will appear more clearly through the following examples, given as an illustration.

EXAMPLE 1

Characterization of a Marine Lecithin Extract in a Fatty Phase

A marine lecithin extract used according to the present invention can be, for instance, the extract marketed by the laboratory Phytobiolab under the brand "OEMINE MER™". It is recommended as a food supplement, with as main indication a preventive action on the cardiovascular system and the nervous system, which are the usual indications for omega 3. The dermatologic indication was unknown until now.

The extract contains 20 percent marine lecithin from wild cold water fish. Marine lecithin contains the following phospholipids: about 45% phosphatidylcholine esterified by the DHA, 20% phosphatidylethanolamine, 16% phosphatidylinositol, 5% phosphatidylserine and 5% sphingomyeline.

The esterified phospholipids are combined with docosahexanoic acid (DHA) in a proportion of 60%, and with eicosapentanoic acid (EPA) in a proportion of 30%. The docosapentanoic acid (DPA) is present at a rate of about 1%, and the alkyl glycerol-type fatty acid at a rate of about 5%. The fatty phase is composed of fish ou comprising 34% omega 3.

The extract is encapsulated in 500 mg doses in the form of gelatine capsules, according to known galenical techniques. Neither additive nor excipient is added. The tocopherols naturally present in the oil play the role of antioxidant. Each capsule contains a useful dose of 100 mg lecithin.

EXAMPLE 2

The effect of a regular intake of marine lecithin on psoriasis has been demonstrated by a recent study which results are presented in tables 1 and 2.

The trials have been performed among a sample of 20 patients, 10 men and 10 women, aged 17 to 71. Every form of psoriasis is represented: plaque psoriasis, scalp psoriasis, guttate psoriasis, erythrodermic psoriasis and reversed psoriasis.

The treatment consisted of 4 capsules per day in two intakes, that is a daily dosage of 0.4 g lecithin.

All the patients who have been receiving the treatment, have seen their lesions regressing gradually in two to four months, and healed completely in four to six months. None of the usual treatments for psoriasis have been used during this study, in a way that the results obtained can only be attributed to lecithin.

Tables legend:

Slight improvement: +

Significant improvement: ++

Complete vanishing of clinical signs:

EXAMPLE 2a

Table 1 presents the results obtained in the treatment of the 6 patients affected by a psoriasis appeared less than 6 years ago.

TABLE 1

| Length of the disease | Clinical observations after treatment | | | | |
| --- | --- | --- | --- | --- | --- |
| | 1 month | 2 months | 3 months | 4 months | 6 months |
| 3 years | ++ | | | +++ | |
| 5 years | + | | | ++ | +++ |
| 1 month | | ++ | | +++ | |
| 6 months | + | +++ | | | |
| 4 years | | | +++ | | |
| 2 years | | | | + | +++ |

EXAMPLE 2b

Table 2 presents the results obtained in the treatment of 14 patients affected by psoriasis for over 5 years Clinical observations after treatment

| Length of the disease | 1 month | 2 months | 3 months | 4 months | 6 months |
| --- | --- | --- | --- | --- | --- |
| 47 years |  | + |  | +++ |  |
| 28 years |  |  |  |  | ++ |
| 54 years |  |  |  |  | +++ |
| 15 years |  | ++ |  | +++ |  |
| 10 years |  | ++ |  |  |  |
| 24 years |  |  | + |  | ++ |
| 20 years |  |  |  |  | +++ |
| 17 years |  | ++ |  | +++ |  |
| 13 years |  |  | ++ |  |  |
| 20 years |  | + |  |  | ++ |
| 6 years | + | ++ |  |  |  |
| 10 years |  | + |  | ++ |  |
| 18 years | + | + |  | + |  |
| 25 years |  | + |  |  | +++ |

Over a total of 14 followed up patients, an improvement has been noticed in all of them from the third month of treatment. The improvement is slight in 64% of the patients (9/14), and significant in 36% (5/15).

After 6 months, 43% have completely recovered (6 patients), 3 of them after only a 4 months cure. In all the other patients, that is 57%, the improvement of the condition is significant after 6 months. From the third month of treatment, a significant improvement or a complete vanishing of the patches is observed in 67% of the patients (4/6) and a slight improvement of the clinical status in 33% (2/6). After 6 months, there is 100% complete recovery.

EXAMPLE 3

The beneficial effect of the use of lecithin according to the invention is illustrated by the clinical case studies below.

Unless otherwise stated, after the first consultation all the patients have received a treatment consisting in 4 capsules of 0.5 g at 20% lecithin per day in 2 intakes, that is a daily dose of 0.4 g lecithin.

Observation 1

Patient aged 59. Psoriasis since age 12 (47 years) with no recovery, except two remissions one during pregnancy and the other during a phototherapy cure 4 years ago, with a partial remission immediately followed by a recurrence.
  $1^{st}$ consultation: the lesions are widespread, in belt, on the elbows and on the edge of the scalp, and appear as large scaly patches which are not very pruriginous.
  $2^{nd}$ consultation (2 months later): The patches have improved.
  $3^{rd}$ consultation (4 months later): all the patches have completely vanished.

Observation 2

Patient aged 52. Psoriasis for 28 years on the elbows, scalp and genitals. Followed up for 20 years with no remission, with local care and fish oil intake 'Biosaumon' since 1988.
  $1^{st}$ consultation: inflamed and scaly psoriasis on the elbows, pruritic on the scalp.
  $2^{nd}$ consultation (6 months later): significant improvement of the patches.

Observation 3

Patient aged 43. Psoriasis appeared 4 years ago, treated with corticoids and phototherapy. No remission. Localized to the elbows, knees, mediothoracic region, scalp.
  $1^{st}$ consultation: spreading psoriasis, very inflammatory, localized to the thorax, elbows, knees and scalp.
  $2^{nd}$ consultation (1 month later): significant improvement of the patches.
  after 4 months treatment, ail the patches have completely vanished.

Observation 4

Patient aged 66. Old psoriasis, since age 12 (54 years), generalized, except on the scalp.
Followed up in St Louis Hospital, Paris. She declares having tried everything, without any result.
  $1^{st}$ consultation: widespread lesions, guttate, not very scaly, with no itching and a little irritation. Localized mainly in the lower limbs, arms and buttocks.
  $2^{nd}$ consultation (6 months later): all the patches have vanished.

Observation 5

Patient aged 39. Psoriasis appeared 2 years ago after a streptococcal tonsillitis. Guttate, treated with corticoids, with no remission, associated with arthritis.
  $1^{st}$ consultation: spreading psoriasis, very inflammatory, guttate, localized to the thorax, elbows, knees chest and scalp, associated with an arthritis localized to the distal interphalanx of both hands, and to the elbows and ankles.
  $2^{nd}$ consultation (1 month later): significant improvement of the patches. Few still remain, but the arthritis continues.
  $3^{rd}$ consultation (4 months later): only a few patches remain on the thorax. The knees are less painful.
  $4^{th}$ consultation (6 months later): the skin has completely recovered, but the arthritis continues.

Observation 6

Patient aged 32. Old psoriasis, guttate, since age 17 (15 years). Appeared suddenly during the summer. Declares having already tested everything: PUVAtherapy, corticotherapy, with poor results.
  $1^{st}$ consultation: guttate lesions over the whoie thorax and legs, with confluent plaques in the mediothoracic region. About a hundred elements on the anterior part alone, and twice as much on the posterior part of the thorax.
  $2^{nd}$ consultation (2 months later): significant improvement. The lesions are clearing. On the back there are two times less lesions. The confluent plaques on the thorax are cured, the ones that aren't completely are clearing from the centre to the periphery.
  $3^{rd}$ consultation (4 months later): total vanishing of all the patches. The patient tried stopping the treatment for 10 days and the lesions tended to reappear on the legs. He takes himself nothing more than two capsules daily.

Observation 7

Patient aged 17. Psoriasis for 10 years, generalized, guttate, appeared after his dog died.
  $1^{st}$ consultation: guttate lesions on the thorax
  $2^{nd}$ consultation (2 months later): the patches have cleared.

Observation 8

Patient aged 30; Old psoriasis, since age 6 (24 years), in friction areas, with a severe psoriatic arthritis. Treated with local corticoids and vitamin D, without any noticeable remission.
  $1^{st}$ consultation: very thick lichenoid patches on the back of the hands and elbows, with erythemo-scaly plaques disseminated on the legs. Thick scales, associated to psoriatic arthritis on the interphalanx of both hands, feet, and ankles which are very inflamed.

2$^{nd}$ consultation (3 months later): slight improvement of the patches, especially on the legs. She mentions the vanishing of digestive disorders she had. The arthritis has improved.

3$^{rd}$ consultation (6 months later): very significant improvement of all the patches.

Especially the ones on the legs, which are in a healing process. The others, more lichenoid in particular on the hands and elbows, have distinctly thinned.

Observation 9

Patient aged 62. Psoriasis on the back for 20 years. The patches have completely vanished after a 6 month treatment.

Observation 10

Patient aged 47. Old psoriasis since age 30 (17 years) localized to the elbows, skin folds, navel. 5 years PUVA-therapy without complete remission.

1$^{st}$ consultation: lesions on the elbows, knees, navel. White, thick skin on reddish bottom, thick scales, rough, infiltrated.

2$^{nd}$ consultation (2 months later): good improvement. The skin is two times less thick.

The whitish layers have vanished and the reddish skin looks less infiltrated. The periphery of the lesions is less irritated and begins healing. Centripetal elution towards recovering.

3$^{rd}$ consultation (4 months later): All the lesions have healed.

Observation 11

Patient aged 50. Ancient psoriasis for 13 years on the scalp and behind the ears. Corticoid treatment with constant recurrence.

1$^{st}$ consultation: lesions behind the ears and on the scalp, not very extended but pruritic.

2$^{nd}$ consultation (3 months later): good improvement. The skin is half as thick, the lesions have disappeared but digestive troubles are persisting.

Observation 12

Patient aged 54. Old psoriasis for 20 years, plaque and inversed. No improvement despite the corticoids, then treated with fish oil for 4 years with slight improvement.

1$^{st}$ consultation: lesions on the pubis, on guteal folds with anal pruritis, on the leg. Large scaly patches, very pruritic and irritated with excoriations.

2$^{nd}$ consultation (2 months later): good improvement. The skin is half as thick, slight improvement, especially on the leg's patch.

3$^{rd}$ consultation (4 months later): all the lesions have healed.

Observation 13

Patient aged 41. Psoriasis for 1 month, generalized after worrying for an exam. The whole thorax and the legs are affected. No improvement despite the corticoids.

1$^{st}$ consultation: The lesions are generalized on the whole thorax and on the right leg. Not very thick but inflamed.

2$^{nd}$ consultation (2 months later): The patches are in a healing process. They have dried. The leg is half healed.

3$^{rd}$ consultation (4 months later): all the lesions have healed.

Observation 14

Patient aged 71. Generalized psoriasis for 6 months, on the whole body with eczematization and secondary infection of the lesions with *staphylococcus aureus*. Treated with local and systemic corticoids with no results. Some patches, especially on the lower limbs, are prone to exudation.

The lesions are associated to a lymphangitis of the right lower limb.

1$^{st}$ consultation: the lesions are widespread, the patient is in tears, can not stand the stinging any longer. An antibiotherapy is prescribed, combined with a cure of lecithin at a dose of 2 capsules morning and evening.

2$^{nd}$ consultation (1 month later): significant improvement. There is no more exudation nor oedema, the patches are beginning to clear from the centre to the periphery. They are not spreading any more. The patient is less tired. The antibiotherapy is stopped and the lecithin treatment is continued with 4 capsules per day.

3$^{rd}$ consultation (2 months later): total vanishing of the patches. The healing of the skin is complete, with no marks. A few areas remain slightly inflamed.

Observation 15

Patient aged 44. Psoriasis appeared 6 years ago after a parting, treated with corticoids and PUVA therapy.

1$^{st}$ consultation: widespread erythrodermic psoriasis, thick scales particularly inflamed, burnt skin with no space of healthy skin, localized to the whole trunk, in belt from hips to ribs, and from elbows to wrists, inflamed, stinging.

2$^{nd}$ consultation (1 month later): same localization but few scales. The skin is less irritated.

3$^{rd}$ consultation (2 months later): complete vanishing of the patches. Only a few small lesions on the periphery of the patches remain. The skin has cicatrized completely with no mark, and is supple and well hydrated.

Observation 16

Patient aged 53. Psoriasis for over 10 years, widespread especially on the buttocks and elbows.

1$^{st}$ consultation: widespread lesions, in particular two large and very thick plaques on the elbows.

2$^{nd}$ consultation (2 months later): the plaques have improved, they have notably thinned.

3$^{rd}$ consultation (4 months later): all the patches have almost vanished.

Observation 17

Patient aged 30. Plaque psoriasis for 4 years.

1$^{st}$ consultation: the lesions are limited: elbows, tibial crest, not very thick.

2$^{nd}$ consultation: the plaques have vanished after 2 months treatment.

Observation 18

Patient aged 16. Psoriasis for 2 years on the scalp, treated with corticoids with poor results.

1st consultation: widespread lesions, on the whole scalp, with large scaly plaques.

2$^{nd}$ consultation (4 months later): the plaques are getting better, they have stopped extending. The dosage is divided by half.

3$^{rd}$ consultation (6 months later): the patches have completely vanished.

Observation 19

Patient aged 32. Old psoriasis since age 14 (18 years), generalized, including the scalp with sheathing lesions, appeared after a severe tonsillitis. All the treatments have been tried, unsuccessfully.

1st consultation: The lesions are widespread, the skin is thick and infiltrated, not very scaly, excoriated. Localized essentially to the lower limbs, with no space of healthy skin.

2nd consultation (1 month later): beginning of a slight improvement. The skin is less infiltrated.

3rd consultation (2 months later): healthy areas are beginning to appear, the skin is more supple, less irritated, less itching (pruritic). Moreover, the patient has noticed an increase of her sweating, which used to be very low even in summer.

4th consultation (4 months later): remarkable evolution. Only a few excoriations remain as well as a few areas which are a little infiltrated, but no more scales.

Observation 20

Patient aged 70. Ancient psoriasis for 25 years, extending despite an intake of Soriatane™ which he can't tolerate any longer. Treated at first with local cares, but with no real improvement, then with fish oil, with poor results either.

1st consultation: very extended lesions, elbows-knees, large patches on the buttocks and on the liver region, scaly, with no itching and a little irritated. Also localized to the scalp.

2nd consultation (2 months later): the patches have improved, they have stopped extending.

3rd consultation (6 months later): the patches have vanished.

The invention claimed is:

1. A method for treatment of conditions induced by, or appearing in the form of scaly or keratosic abnormal formations of the derma, selected from the group consisting of common psoriasis, guttate psoriasis, nummular psoriasis, plaque psoriasis, erytrhodermic psoriasis, psoriatic arthritis, pustular psoriasis, child psoriasis, parapsoriasis, and chronic and acute dermatitis, comprising administering a medication comprising at least one of a lecithin and a lecithin rich extract, orally, rectally or via direct lymphatic route,
    said lecithin comprising phospholipids, in an amount by weight of total phospholipids:
    from 10% to 75% phosphatidylcholine;
    from 10% to 30% phosphatidylinositol;
    from 5% to 30% phosphatidylethanolamine;
    from 5% to 20% phosphatidylserine;
    from 5% to 30% sphingomyeline,
    said phospholipids being esterified by Omega 3-type fatty acids.

2. Method according to claim 1, wherein said lecithin rich extract comprises lecithin in a amount of 10-50% by weight, in a fatty phase.

3. Method according to claim 1, wherein said lecithin comprises, by weight:
    45% phosphatidylcholine;
    16% phosphatidylinositol;
    20% phosphatidylethanolamine;
    10% phosphatidylserine; and
    5% sphingomyeline.

4. Method according to claim 1, wherein said phospholipids are esterified by fatty acids, in an amount by weight of total fatty acids:
    docosahexaenoic acid within a range of 15% to 85%;
    eicosapentaenoic acid within a range of 5% to 35%;
    docosapentaenoic acid within a range of 0.5% to 5%; and
    a fatty acid of the alkyl glycerol type within a range of 5% to 30%.

5. Method according to claim 4, wherein said phospholipids are esterified by the fatty acids, in an amount by weight of total fatty acids:
    docosahexaenoic acid at least 17%;
    eicosapentaenoic acid at least 14%;
    docosapentaenoic acid at least 0.5%; and
    the fatty acid of the alkyl glycerol type at least 5%.

6. Method according to claim 1, wherein said lecithin is lecithin extracted from a marine organism selected from the group consisting of fish, shrimps, krill, zooplankton, algae, phytoplankton, and mixtures thereof.

7. Method according to claim 2, wherein said fatty phase comprises a fish oil.

8. Method according to claim 7, wherein the fish oil comprises an Omega-3 rich fish oil.

9. Method according to claim 1, wherein said medication is administered orally.

* * * * *